United States Patent [19]

Kellett

[11] Patent Number: 4,806,572
[45] Date of Patent: Feb. 21, 1989

[54] HYDROPHILIC FOAM PAD FOR MAKEUP REMOVAL

[75] Inventor: George W. Kellett, Cranford, N.J.

[73] Assignee: Creative Products Resource Asociates, Ltd., Clifton, N.J.

[21] Appl. No.: 46,847

[22] Filed: May 4, 1987

[51] Int. Cl.$^4$ .................... C08G 18/30; C08K 9/06
[52] U.S. Cl. .................. 521/112; 521/116; 521/130; 521/159; 521/163; 521/167; 521/172; 521/905; 424/78; 424/486; 424/401; 252/91
[58] Field of Search .............. 424/486, 28, 78; 521/112, 116, 130, 159, 163, 167, 172, 905

[56] References Cited

U.S. PATENT DOCUMENTS

| | | | |
|---|---|---|---|
| 3,088,158 | 5/1963 | Boyle et al. | 15/506 |
| 4,066,394 | 12/1974 | Leonard | 8/137 |
| 4,127,515 | 11/1978 | MacRae et al. | 521/112 |
| 4,137,200 | 1/1979 | Wood et al. | 521/159 |
| 4,271,272 | 6/1981 | Strickman et al. | 521/110 |
| 4,343,910 | 8/1982 | Busch, Jr. et al. | 521/82 |
| 4,548,954 | 10/1985 | Smith et al. | 521/52 |
| 4,563,483 | 1/1986 | Smith et al. | 521/111 |
| 4,565,644 | 1/1986 | Smith et al. | 252/94 |
| 4,569,861 | 2/1986 | Smith et al. | 427/244 |
| 4,581,385 | 4/1986 | Smith et al. | 521/111 |
| 4,594,362 | 6/1986 | Smith et al. | 521/52 |

FOREIGN PATENT DOCUMENTS 2015972 4/1970 France .

*Primary Examiner*—John Kight
*Assistant Examiner*—S. A. Acquah
*Attorney, Agent, or Firm*—Merchant, Gould, Smith, Edell, Welter & Schmidt

[57] ABSTRACT

A makeup remover pad is provided which comprises a resilient, open-celled hydrophilic foam matrix, wherein said matrix integrally incorporates an aqueous phase incorporating about 25–75% water, about 15–70% of a water-insoluble emollient oil, and an amount of surfactant effective to stabilize the aqueous phase so that it is released from the foam matrix as a homogeneous emulsion when the pad is applied to skin.

20 Claims, No Drawings

HYDROPHILIC FOAM PAD FOR MAKEUP REMOVAL

BACKGROUND OF THE INVENTION

Cosmetic formulations which are commonly referred to as "makeup", include mascara, eye shadow, eyeliner, blush, lipstick and various foundation bases. Makeup compositions usually employ a waxy base, such as beeswax, carnauba wax, paraffin, lanolin derivatives, or mixtures thereof. The base acts to suspend and bind various coloring agents, e.g., mineral dyes and metal powders.

Since these compositions are usually highly adherent and water-resistant, a number of products have been designed to remove makeup from the skin. These products include cloth pads which have been premoistened with various liquid compositions which are intended to solubilize and absorb makeup. These compositions include emulsions of mineral oil in water (Take Off ®, Personal Products Co., Milltown, N.J.) and nonaqueous mixtures of emollient esters with mineral oil (Almay ® eye makeup remover pads, Beatrice Co., New York, N.Y.).

However, such premoistened products suffer from a number of disadvantages. The amount of liquid released onto the skin is difficult to control. The aqueous formulations can run or irritate the eyes of the user, and the oil-based products can leave the skin greasy or sticky.

Therefore, a need exists for a premoistened applicator which can deliver a controlled amount of a makeup removal formulation to the skin of the user. A further need exists for a premoistened applicator which effectively removes makeup without unduly wetting or oiling the skin of the user or irritating the eyes.

SUMMARY OF THE INVENTION

The present invention is directed to a makeup remover which comprises a shaped body of a resilient, open-celled hydrophilic polyurethane foam. The polyurethane foam is formed by reaction of selected prepolymer resins with an aqueous phase, which becomes integrally incorporated into the cell walls of the cured foam matrix. This "interior aqueous phase" is formulated to contain large amounts of emollient oils which act as solvents for the waxy makeup components. The oils are emulsified in the aqueous phase with relatively small amounts of surfactants. For example, the interior aqueous phase can contain up to 60-70% by weight of emollient oils, such as a mixture of mineral oils and fatty acid esters, and as little as 30-40% water and 5-10% surfactant. Liquid blends of this type often do not afford stable emulsions under ambient conditions. However, it was surprisingly found that the interior aqueous phase in the present pads is stabilized by the foam matrix to the extent that it is released from the foam as a homogeneous emulsion when the pad is applied to the skin.

Preferred foam pads prepared in accord with the invention are resilient and possess a fine open-celled matrix. These characteristics permit the pad to remain essentially dry to the touch, yet to release an amount of the interior aqueous phase effective to solubilize and disperse makeup when it is wiped over the skin.

It is also advantageous to incorporate a minor amount of an inorganic salt such as sodium chloride into the aqueous phase. Surprisingly, it was found that about 0.05-1.5% of NaCl substantially increased the amount of the aqueous phase which was released from the foam matrix during use, without unduly irritating the skin of the user.

The small cell-size imparts a high degree of slip to the pads while the substantially integral incorporation of the interior aqueous phase into the foam matrix leaves the open cellular voids largely clear and available to absorb the solubilized makeup components. The skin is left clean and slightly moistened by the action of the emollient oils. The use of an aqueous dispersion of emollient oils to foam the prepolymer resin also completely eliminates the need to post-add water or other cleaning liquids to the preformed foams. In contrast to foam pads such as the wax-containing pad disclosed by McRae et al. (U.S. Pat. No. 4,127,515), which must be moistened prior to use, the addition of water to the present pads would be deleterious in that the added water would dilute and could act to destabilize the interior aqueous phase. Furthermore, the excess water would destroy the ability of the present pad to release the interior aqueous phase in a controlled fashion, leading to dripping and running during use.

As used herein, the term "pad" is intended to encompass any shaped foam body which is useful for makeup removal by manual application to the skin, including sticks, sheets and discs of hydrophilic foam. The term "resilient" is intended to indicate that the pads maintain their integrity during use, e.g., are not friable. All percentages are weight percentages unless otherwise indicated. Percentages of commercially-available materials, such as emollient oils have been adjusted downward, if necessary, so that they represent only the active component or components, and do not include water or other solvents.

DETAILED DESCRIPTION OF THE INVENTION

The makeup remover pads of the present invention are prepared by a process comprising forming an aqueous dispersion comprising an emollient oil, a nonionic surfactant, and optionally, an inorganic salt. The fully-formed aqueous dispersion is then combined with a water-foamed prepolymer resin and the reaction mixture allowed to foam and cure to yield a self-cross-linked, open-celled, resilient polyurethane foam body. The foam may be cured to the desired final shape in an appropriately formed mold, or may be cut into the en-duse configuration from a larger body.

Prepolymer Resins

A commercially-available class of water-foamable prepolymer resins which yield cross-linked, hydrophilic polyurethane foams upon the addition of stoichiometric excesses of water are those belonging to the Hypol ® series (W. R. Grace & Co., Lexington, MA; FHP 5000, 4000, 3000, 2000, 2000 HD, 2002) which are generally described in U.S. Pat. No. 4,137,200 and in the W. R. Grace & Co. technical bulletins, *Hypol* ® and *Hypol Plus* ® *foamable hydrophilic prepolymers,* the disclosures of which are incorporated by reference herein. These liquid resins are prepared by capping mixtures of low molecular weight polyols having 3-8 hydroxyl groups and polyoxyethylene diols with toluene diisocyanate. The capped alcohol mixtures have an average number of free isocyanate groups per molecule which is equal to two or more, e.g., 2-8.

These resins possess molecular weights within the range of about 1300-1400 and have about 1.5-2.6 mEq./g. of free isocyanate groups. Upon being contacted with molar excess of water, the isocyanate groups hydrolyze to release carbon dioxide gas, thus foaming the resin without the need for added catalysts or blowing agents. The free amino groups formed by the hydrolysis reaction react with unhydrolyzed isocyanate groups to form ureido groups which cross-link and stabilize the foam, while entrapping a part of the excess water in the cell walls, where it acts to impart hydrophilic properties to the foam. The compatibility of the foam matrix with large molar excesses of water is a necessary requirement of resins useful in the practice of the present invention, since large amounts of water are needed to uniformly introduce large amounts of hydrophobic emollient oils into the matrix.

Other poly-$C_2$-$C_3$-alkylenoxy glycols capped with aromatic isocyanates may be prepared which possess a suitable balance between their extent of cross-linking prior to foaming and their ability to cross-link or to further cross-link during foaming (due to the presence of more than two reactive isocyanate groups per resin molecule), so as to be useful in the practice of the present invention over the entire range of oil and surfactant content. These prepolymer resins are prepared by polymerizing ethylene oxide to yield polyalkylenoxy polyols having a molecular weight of about 900–1100. These polyols are reacted with a stoichiometric excess of a polyisocyanate. Suitable isocyanates include toluene diisocyanate, triphenylmethane-4,4',4"-triisocyanate, benzene-1,3,5-triisocyanate, hexamethylene diisocyanate, xylene diisocyanate, chlorophenylene diisocyanate and mixtures thereof. The useful resins recovered have a somewhat lower number of mEq of free isocyanate groups (NCO) per gram of resin than do the Hypol® resins, e.g., 1.3–1.5 mEq/gram and can exhibit substantially higher tensile strengths when foamed and cured at ambient temperatures.

Commercially-available self cross-linking resins include Trepol® A-62 and TRE STD® prepolymer resin (Twin Rivers Engineering Co., East Booth Bay, ME), which form acceptable foams upon reaction with at least a stoichiometric excess of water without employing a low molecular weight polyol component to raise the average number of free isocyanate groups per glycol ether molecule to above two. TRE STD® resin has an average free isocyanate content of about 1.4 mEq./gram, comprises a polyol component having an average molecular weight of about 1000, exhibits a viscosity at 32° C. of 4700 cps and solidifies at 15.5° C.

In the practice of the present invention, useful foams may be formed employing a weight ratio of water to prepolymer resin of about 0.5–4:1, preferably about 0.75–3.5:1. These ranges represent mole ratios of water to free isocyanate groups of about 20–150:1, preferably about 30–135:1.

These amounts of water react with the free isocyanate groups to release carbon dioxide which blows the prepolymer into a cross-linked, open-celled foam which is rendered hydrophilic by entrapment of excess water in the cell walls of the foam matrix. When the prepolymer-slurry mixture is allowed to set in molds, a flexible, resilient foam body of the desired shape is formed.

Emollient Oils

Useful emollient oils for incorporation into the aqueous reactant phase include those water-insoluble liquids which can effectively solubilize the natural and synthetic waxes typically employed as makeup bases. These oils also function to soften the skin of the user and provide a degree of barrier protection against environmental irritants.

Preferred emollient oils for use in the present invention include mixtures of (a) inorganic emollient oils (mineral or silicone oils) with (b) emollient organic esters. Mineral oils are complex mixtures of paraffin and naphthalene hydrocarbons, e.g., the $C_{18}$–$C_{36}$ hydrocarbon mixtures available from Penreco, Butler, Pa., e.g., Peneteck® technical mineral oil (viscosity 3.4–4.7 centistokes @40° C.), the Drakeol® light mineral oils, USP (viscosities 6.5–30.2 centistokes @40° C.) and the Drakeol® mineral oils, USP (viscosities 35.0–70.0 @40° C.). The specific gravity of mineral oils useful in the practice of the present invention preferably is about 0.80–0.9 at 15.6° C. (60° F.). Preferred mineral oils for use in the present pads are odorless, colorless (30+Saybolt color) and comply with FDA requirements under the Federal Food, Drug and Cosmetic Act.

Silicone fluids can also be used alone or in combination with the mineral oil component. These fluids also function to break up films of waxy or greasy makeup. Useful classes of silicone fluids include the linear polydimethylsiloxanes or the tetrameric or pentameric cyclic siloxanes (cyclomethicones) which are available from Rhone-Poulenc, Inc. (Monmouth Junction, N.J.) as the Rhodorsil® fluid series in a wide range of viscosities (i.e., 10–10,000 cps.). When used as a component of the aqueous reactant phase, fluids of about 0.5–150 cps viscosity, preferably about 25–100 cps, are preferred. Preferably, mineral oil and/or silicone oil will make up about 5–45%, most preferably about 25–40%, of the total aqueous phase.

Preferred emollient esters include ($C_5$–$C_{30}$)alkyl ($C_8$–$C_{22}$) fatty acid esters, wherein the fatty acid moiety is optionally substituted with a ($C_8$–$C_{22}$)alkanoyl group. Such esters are commercially-available, e.g., as Ceraphyll® 847 [2-octyl(dodecyl)](12-steroyl-stearate), Ceraphyll® 368 (2-ethylhexylpalmitate) and Ceraphyll® 230 (isocetyl stearate) from Van Dyk & Co., Belleville, N.J. Preferably, the aqueous reactant phase will include about 5–50% by weight of these fatty acid esters, most preferably about 10–45%.

Other useful classes of water-insoluble emollient esters include the benzyl alcohol esters of one or more $C_{10}$–$C_{20}$ fatty acids, e.g., benzyl linoleate (Dermol® 618, Alzo, Inc., Matawan, N.J.); the fatty alcohol esters of benzoic acid such as the $C_{12}$–$C_{15}$ alkylbenzoates (Finsolv® TN, Finetex, Inc.) described in U.S. Pat. Nos. 4,278,655 and 4,275,222; the liquid fatty alcohol esters of $C_3$–$C_6$ aliphatic carboxylic acids, i.e., isodecyl neopentanoate (Dermol® 105); and the ($C_1$–$C_5$)alkanol di- or tri- esters of dimer or trimer acid (the dimer or trimer of oleic acid). Such esters are commercially available as Schercemol® TT (triisopropyl trimerate) and Schercemol® DID (diisopropyl dimerate, Scher Chemicals, Clifton, N.J.). The liquid fatty acid-esters of dimer acid may also be successfully employed in the present compositions, e.g., the diisostearyl ester of dimer acid, Schercemol® DISD. The liquid esters of polyethylene glycol, e.g., the polyethylene glycols of average molecular weight of about 300–600, may also be employed.

The aqueous reactant phase will incorporate about 15–70%, preferably about 25–65%, and most preferably, about 35–55%, total emollient oils. The ratio of mineral and/or silicone oil:ester can be about 1:1. However, the aqueous reactant phase can be (a) "high mineral/silicone oil" (about 20–45%, preferably about 25–40% mineral and/or silicone oil)—"low ester" $\leq$10% esters, e.g., about 1–9% ester) or (b) "low mineral/silicon oil" (about 5–20%, preferably about 7.5–15% mineral and/or silicone oil)—"high ester" (about 10–50% ester, preferably about 15–45% ester).

Surfactant

One or more foam-reticulating surfactants will also be incorporated into the aqueous phase. These surfactants function to remove the window membranes of the foam cells, thus producing the desired reticulated, or highly open, structure. The surfactant functions to stabilize the oil-water emulsion which is incorporated into the foam so that it is released as a homogeneous emulsion during use. The surfactant also enhances the cleaning power of the foam by dispersing waxes when the foam is brought into contact with a layer of makeup. Foam reticulating surfactants are preferably selected from nonionic surfactants, anionic surfactants, or mixtures thereof, which are soluble or dispersible in water.

Nonionic surfactants are the preferred surfactants for use in this invention. This class of surfactants includes the block copolymers formed by condensing ethylene oxide with a hydrophobic polyxoyalkylene base formed by the condensation of propylene oxide with propylene glycol. The hydrophobic portion of these compounds has a molecular weight sufficiently high so as to render it water-insoluble. The addition of polyoxyethylene moieties to this hydrophobic portion increases the water solubility of the molecule as a whole, and the liquid character of the product is retained up to the point where the polyoxyethylene content is about 50% of the total weight of the condensation product. Examples of compounds of this type include certain of the commercially-available Pluronic ® surfactants (BASF Wyandotte Corp., Wyandotte, Mich.), especially those in which the polyoxypropylene ether has a molecular weight of about 1500–3500 and the polyoxyethylene content is about 15–35% of the molecule by weight, i.e., Pluronic ® L-62, L-72 and L-92.

Another preferred class of nonionic surfactants is the fatty acid esters of $C_2$–$C_5$-polyols, e.g., the ($C_8$–$C_{22}$-)fatty acid monoesters of glycerol, propylene glycol, ethylene glycol, sorbitol, and the like. For example, glyceryl monostearate is commercially-available as Cerasynt ® 945 from Van Dyk & Co., Belleville, N.J.

Other useful nonionic surfactants include the condensation products of $C_8$–$C_{22}$ alkyl alcohols with 2–50 moles of ethylene oxide per mole of alcohol. Examples of compounds of this type include the condensation products of $C_{11}$–$C_{15}$ fatty alcohols with 3–50 moles of ethylene oxide per mole of alcohol which are commercially-available from Shell Chemical Co., Houston, Tex. as, i.e., Neodol ® 23-6.5 ($C_{12}$–$C_{13}$ fatty alcohol condensed with about 7 moles of ethylene oxide), the Poly Tergent ® SLF series from Olin Chemicals or the Tergito ® series from Union Carbide, e.g., Tergitol ®15-S-15, which is formed by condensing about 15 moles of ethylene oxide with a $C_{11}$–$C_{15}$ secondary alkanol; and Tergitol ® TMN-6, which is the condensation product of about 6 moles of ethylene oxide with isolauryl alcohol (CTFA name: isolaureth-6). Another commercially-available nonionic surfactant of this class is the condensation product of lauryl alcohol with about 11–40 moles of ethylene oxide, e.g., Lipocol ® L-23 ($OEt_{23}$)(Lipo Chemicals, Inc., Patterson, N.J.).

Other nonionic surfactants which may be employed include the ethylene oxide esters of $C_6$–$C_{12}$ alkyl phenols such as (nonylphenoxy)polyoxyethylene ether. Particularly useful are the esters prepared by condensing about 8–12 moles of ethylene oxide with nonylphenol, i.e., the Igepal ® CO series (GAF Corp., New York, N.Y.).

Other useful nonionics include the ethylene oxide esters of alkyl mercaptans such as dodecyl mercaptan polyoxyethylene thioether, the ethylene oxide esters of fatty acids such as the lauric ester of polyethylene glycol and the lauric ester of methoxypolyethylene glycol, the ethylene oxide ethers of fatty acid amides, the condensation products of ethylene oxide with partially fatty acid esters of sorbitol such as the lauric ester of sorbitan polyethylene glycol ether, and other similar materials, wherein the mole ratio of ethylene oxide to the acid, phenol, amide or alcohol is about 5–50:1.

Useful anionic surfactants include the alkali metal salts or sulfated ethylenoxy fatty alcohols (the sodium or ammonium sulfates of the condensation products of about 1–4 moles of ethylene oxide with a $C_{12}$–$C_{15}$ n-alkanol, i.e., the Neodol ® ethoxysulfates, such as Neodol ® 25-3S, Shell Chemical Co.): anionic detergent salts having alkyl substituents of 8 to 22 carbon atoms such as the water-soluble higher fatty acid alkali metal, ammonium or amine soaps, e.g., sodium myristate and sodium palmitate.

Preferred compounds of this class include the trialkanol amine salts, e.g., the triethanol amine fatty acid salts. These compounds can be formed in situ in the mildly basic (pH 7–8.5) aqueous phase by reaction of a ($C_8$–$C_{22}$) fatty acid or a mixture thereof with triethanol amine (TEA). For example, TEA stearate and TEA palmitate can be formed by a mixture of Neofat ® 18-55, a mixture of stearic and palmitic acids, with TEA during the formation of the aqueous reactant phase.

Another useful class of anionic surfactants encompasses the water-soluble sulfated and sulfonated anionic alkali metal and alkaline earth metal detergent salts containing a hydrophobic aromatic moiety (typically containing from about 8 to 22 carbon atoms) such as salts of mono- or polynuclear aryl sulfonates having from abut 0 to 16 carbon atoms in the alkyl group, e.g., sodium xylene sulfonate and sodium toluene sulfonate, sodium naphthalene sulfonate and the like. Sodium dodecylbenzenesulfonate, magnesium tridecylbenzenesulfonate and lithium or potassium pentapropylenebenzenesulfonate are available as the Bio-Soft ® series, i.e., Bio-Soft ® D-40 (Stephan Chemical Co., Northfield, Ill.). Useful naphthalene sulfonates include the alkali metal salts of alkyl naphthalene sulfonic acids (methyl naphthalene sodium sulfonate, Petro ® AA, Petrochemical Corporation).

Other useful classes of anionic surfactants include the alkali metal salts of sulfonsuccinic acid esters, e.g., dioctyl sodium sulfosuccinate (Monawet ® series, Mona Industries, Inc., Patterson, N.J.); sulfated higher fatty acid monoglycerides such as the sodium salt of the sulfated monoglyceride of coconut oil fatty acids and the potassium salt of the sulfated monoglyceride of tallow fatty acids; alkali metal salts of sulfated fatty alcohols containing from about 10 to 18 carbon atoms (e.g., sodium lauryl sulfate and sodium stearyl sulfate); sodium $C_{14}$–$C_{16}$-alpha-olefin sulfonates such as the Bio-Terge ® series (Stephan Chemical Co.); alkali metal salts of higher fatty esters of low molecular weight alkylol sulfonic acids, e.g., fatty acid esters of the sodium salt of isethionic acid; the fatty ethanolamide sulfates; and the fatty acid amides of amino alkyl sulfonic acids, e.g., lauric acid amide of taurine.

Preferably, the combined amount of nonionic and anionic surfactants in the aqueous reactant phase will be about 1–15%, most preferably about 2.5–10%. The weight ratio of anionic surfactant to nonionic surfactant will be about 1.5–0.75:1, preferably about 1.25–1:1.

Inorganic Salt

It has been found desirable to add a small amount of an inorganic salt to the aqueous reactant phase to facilitate release of the interior aqueous phase from the foam. Such salts include alkali metal and alkaline earth metal salts such as halides, sulfates, carbonates, bicarbonates, phosphates and the like, e.g , NaCl, KCl, LiCl, $CaCl_2$, NaI and the like.

Antimicrobial Agent

Minor but effective amounts of chemically-compatible antimicrobial agents may also be included in the present aqueous phases to reduce or eliminate the bioburden of the foam pads during storage and following exposure to air.

Such agents include $C_1$–$C_5$-parabens (parahydroxy-($C_1$–$C_5$)alkylbenzoates), quaternary ammonium salts (benzalkonium choride, benzethonium chloride, methylbenzethonium chloride cetalkonium chloride) cresol, chlorhexidine digluconate, hydantoin derivatives and the like.

The amount of any given antimicrobial agent or mixture thereof included will be dependent upon its potency and stability, but generally will not exceed about 1.0% by weight of the aqueous phase.

Fragrance

Minor but effective amounts of fragrance selected so as to be chemically-compatible with the above-described ingredients are prefeably included in the compositions of the present invention for cosmetic purposes. Useful fragrances will include, for instance, about 0.025–2% preferably about 0.05–1.5% of floral oils such as rose oil, lilac, jasmine, wisteria, apple blossom or compound bouquets such as spice, aldehydic, woody, oriental and the like.

Preparation

In a typical procedure, an aqueous mixture of the water, the alkanol amine, the water-soluble nonionic surfactant, such as a Pluronic ®, and a portion of the antimicrobial agent is prepared and heated to about 80°–85° C. with stirring. A second "oil phase" mixture is prepared by combining the inorganic emollient oil, the organic ester emollient oil, the fatty acid component of the alkanol amine-fatty acid salt and the partly-water-soluble nonionic surfactant, such as a fatty acid-polyol ester; and heating this ixture at about 80°–85° C. until it becomes homogeneous. The two mixtures are then combined with agitation and heating continued for about 10–30 min. The emulsion is then cooled slowly. Any additional biocide is added at about 50°–65° C. To form "high mineral/silicone oil" aqueous reactant phases, additional inorganic emollient oil can be added to the aqueous reactant phase at about 20°–30° C. If desired, a dilute (e.g., 5–15%) aqueous solution of the inorganic salt is added to the aqueous phase just prior to its reaction with the prepolymer resin.

Therefore, aqueous reactant phases prepared in accord with the present invention will comprise about 25–75%, preferably about 30–65%, and most preferably, about 35–45% water; about 20–70%, preferably about 25–65% and most preferably about 35–60% water-insoluble emollient oil; which oil will preferably comprise a mixture of mineral oil and a fatty acid alkyl ester; about 1–15% of a mixture of anionic and nonionic surfactants in a weight ratio of about 1.5–0.75:1, and optionally, about 0.25–1.5% of an inorganic salt such as NaCl. The aqueous phase will not include any natural or synthetic waxes.

The prepolymer resin is then added to the finished aqueous phase with strong agitation under ambient conditions. The weight ratio of aqueous reactant phase to resin is about 1–3:1, preferably about 1.5–2:1. After brief reaction periods ($\leq$1 minute), the foaming mixture is poured into the apprpprate mold and allowed to cure under ambient conditions, so that it retains essentially all of the water and the other components present in the aqueous phase.

The resultant moist foam pads are ready for use, and are enclosed in moisture and vapor-impermeable packages, such as those formed of metal foil, plastic films or paper-foil, paper-plastic composites. The applicators can be packaged individually or a plurality of sheets can be placed within a single container. Suitable packaging for premoisturized products is known in the art. For example, see U.S. Pat. Nos. 4,017,002; 3,057,467; and 4,219,129, the disclosures of which are incorporated by reference herein.

The invention will be further described by reference to the following detailed examples.

EXAMPLE I

Makeup Remover Pad

Water (740.9 g) was added to a beaker and 4.2 g of triethanol amine added with stirring. The solution was heated to 80°–85° C. and 1.0 g of methyl paraben, 1.0 g propyl paraben, and 8.99 g of Pluronic ® L-62 nonionic surfactant were added with continued stirring. To a second beaker was added 59.85 g of Ceraphyll ® 368, 29.9 g of Ceraphyll ® 847, 29.9 g of Neofat ®18–55 and 89.8 g of Peneteck ® mineral oil. This mixture was heated to 80°–85° C. until it became clear, homogeneous, and free of particulate matter.

The contents of the second beaker were slowly added to the stirred contents of the first beaker at 80°–85° C., and the temperature was maintained for 15 min. Heating was discontinued, and the reaction mixture cooled to 55° C. Germaben II biocide (1.5 g) was added at this point and the reaction mixture cooled to 50° C., at which point 3.0 g of fragrance were added. Stirring was continued until the temperature of the reaction mixture fell to 30°–35° C. Stirring was discontinued until the temperature of the reaction mixture reached 25° C. Stirring was resumed, and 333 g of Peneteck ® mineral oil was added to the reaction mixture, to give a total mineral oil content of 32.1%, a total water content of 55%, and a total organic emollient ester (Ceraphyll ®) content of 6.69%.

Hypol ® 2000 polymer resin (35g) was added to the stirred aqueous reaction mixture (65 g) at 25° C. After ten seconds of vigorous agitation, the foaming reaction mixture was poured into an open cylindrical mold (6.0 cm diameter) and allowed to rise and set under ambient conditions. After 2.0 hours, the foam body was sliced to yield cylindrical pads (6.0 cm wide × 1.0 cm deep).

The resultant pads were composed of a resilient, open-celled foam which were dry to the touch. When applied to clean skin under conditions of pressure, the pad deposited a homogeneous coating of a clear emollient emulsion. When manually applied, the pad readily removed a layer of waterproof mascara (Cover Girl Clean Lash) from the skin without undue sticking or liquid release.

EXAMPLE II

Following the procedure of Example I, with the modification noted, makeup remover pads were made using the aqueous phase-resin combinations listed on Table I, below.

TABLE I

| | Makeup Remover Pads | | | | |
|---|---|---|---|---|---|
| Aqueous Phase Ingredient | A* | B+ | C++ | D** | E+++ |
| | | | Weight Percent | | |
| Water | 57.77 | 70.47 | 47.2 | 38.18 | 32.70 |
| Triethanol Amine | 0.68 | 0.14 | 0.4 | 0.42 | 0.28 |
| Methyl Paraben | 0.1 | 0.07 | 0.1 | 0.1 | 0.07 |
| Propyl Paraben | 0.1 | 0.07 | 0.1 | 0.1 | 0.07 |
| Pluronic ® L-62 | 1.5 | 1.0 | 0.84 | 0.9 | 0.61 |
| Ceraphyll ® 368 | 9.85 | 6.90 | 23.8 | 29.9 | 18.5 |
| Ceraphyll ® 847 | 4.92 | 3.45 | 11.8 | 15.0 | 6.1 |
| Cerasynt ® 945 | 4.92 | 3.45 | 2.98 | 3.0 | 2.1 |
| Neofat ® 18-55 | 4.92 | 3.45 | 2.98 | 3.0 | 2.1 |
| Mineral oil | 14.77 | 10.40 | 8.85 | 8.97 | 6.1 + 23.50 |
| NaCl (10% Aq) | — | — | — | — | 7.5 |
| Germaben II | 0.15 | 0.11 | 0.15 | 0.15 | 0.1 |
| Fragrance | 0.30 | 0.21 | 0.30 | 0.3 | 0.6 |

*Combined with Hypol ® 3000 at 25° C. in a ratio of aqueous phase to resin of 6.5:3.5 or with Hypol ® 2000 in a 5.5:4.5 ratio.
+Combined with Hypol ® 5000 in a ratio of total aqueous phase to resin of 7:3.
++Aqueous phase: Hypol ® 2002 was 6.5-3.5.
+++Prepared according to Example I, NaCl solution added to aqueous phase just prior to mixing with resin.

The pads of Examples A-E performed satisfactorily to remove mascara coatings as described in Example I. The pad of Example IIE was somewhat superior in performance with respect to the ease of release of the interior aqueous phase, which is believed to be due to the 0.75% NaCl content of the pad. The "high oil" (35-60%) pads of Examples I, IIC, IID and IIE were also somewhat more effective than the other pads in ease of use ("slip") and in their ability to solubilize the makeup base.

While certain representative embodiments of the invention have been described herein for purposes of illustration, it will be apparent to those skilled in the art that modification therein may be made without departing from the spirit and scope of the invention.

What is claimed is:

1. A makeup remover pad comprising a resilient, open-celled, hydrophilic polyurethane foam matrix, wherein said matrix integrally incorporates an aqueous phase incorporating about 25-75% water, about 15-70% of a water-insoluble liquid emollient oil, and an amount of surfactant effective to stabilize the aqueous phase so that it is released from the foam matrix as a homogenous emulsion when the pad is applied to skin, and wherein said aqueous phase contains no natural or synthetic wax.

2. The makeup remover pad of claim 1 wherein the surfactant comprises an anionic surfactant:nonionic surfactant mixture in a weight ratio of about 1.5-0.75:1.

3. The makeup remover pad of claim 2 wherein the surfactant mixture comprises about 1-15% of the aqueous phase.

4. The makeup remover pad of claim 1 wherein the emollient oil comprises about 20-45% of mineral oil, silicone fluid or mixtures thereof, and less than about 10% of an organic emollient ester.

5. The makeup remover pad of claim 1 wherein the emollient oil comprises about 5-20% of mineral oil, silicone fluid or mixtures thereof, and about 10-50% of an organic emollient ester.

6. The makeup remover pad of claim 1 wherein the aqueous phase comprises about 0.05-1.5% of an inorganic alkali metal or alkaline earth metal salt.

7. The makeup remover pad of claim 6 wherein the metal salt is sodium chloride.

8. A makeup remover pad prepared by a process comprising:
(a) forming an aqueous reactant phase comprising about 25-75% water, about 25-65% of a water-insoluble lliquid emollient oil and about 1-15% of a mixture of anionic surfactant and nonionic surfactant in a weight ratio of about 1.5-0.75:1, and wherein said aqueous reactant phase contains no natural or synthetic wax; and
(b) mixing said aqueous reactant phase with a water-foamable prepolymer resin which contains at least two free isocyanate groups per resin molecule so that the final mole ratio of water to total free isocyanate groups is about 20-150:1, thereby converting the resin into a resilient, open-celled polyurethane foam body which integrally and releasably incorporates the aqueous reactant phase.

9. The makeup remover pad of claim 8 wherein the weight of the aqueous phase to the prepolymer resin phase is about 1-3:1.

10. The makeup remover pad of claim 8 wherein the aqueous phase comprises about 5-40% mineral oil.

11. The makeup remover pad of claim 8 wherein the aqueous phase comprises about 5-50% of a water-insoluble fatty acid ester.

12. The makeup remover pad of claim 8 wherein the nonionic surfactant comprises a water-soluble polyoxyethylene-polyoxypropylene block copolymer wherein the polyoxypropylene block has a molecular weight of about 1500-3500 and the polyoxyethylene is about 15-35% by weight of the copolymer.

13. The makeup remover pad of claim 8 wherein the nonionic surfactant comprises a polyol-fatty acid ester.

14. The makeup remover pad of claim 8 wherein the anionic surfactant comprises a fatty acid amine salt.

15. The makeup remover pad of claim 8 wherein the aqueous phase comprises about 0.05-1.5% of an inorganic salt which substantially increases the amount of the aqueous reactant phase which is released from the foam when the pad is applied to the skin.

16. A makeup remover pad prepared by a process comprising:
(a) forming an aqueous reactant phase comprising about 30-65% water, about 35-60% of a liquid mixture of mineral oil and a fatty acid ester comprising a ($C_5$-$C_{30}$)alkyl ($C_8$-$C_{12}$)fatty acid ester; and about 2.5-10% of a mixture of (i) a copolymer of ethylene oxide with a polyoxypropylene block having a molecular wieght of about 1500-3500 and (ii) a $C_8$-$C_{22}$ fatty acid mono ester of a $C_2$-$C_5$ polyol; and an anionic surfactant component comprising a fatty acid alkanol amine salt, in a weight ratio of nonionic surfactant component to anionic surfactant component of about 1.25-1:1, and wherein said aqueous reactant phase contains no natural or synthetic wax; and (b) mixing said aqueous reactant phase with a water-foamable prepolymer resin in a weight ratio of aqueous phase to prepolymer of about 2–1.5:1, said prepolymer resin comprising a toluene diisocyanate-capped polyakylenoxy ether comprising about 1.3–2.6 mEeq/g of isocyanate groups, so as to convert said resin into a hydrophilic, resilient, open-celled polyurethane foam body.

17. The makeup remover pad of claim 16 wherein the aqueous phase further comprises about 0.05–1.5% of an alkali metal halide.

18. The makeup remover pad of claim 16 wherein the aqueous phase comprises about 25–40% mineral oil and less than about 10% of the fatty acid ester.

19. The makeup remover pad of claim 16 wherein the aqueous phase comprises about 5–20% mineral oil and about 10–50% of the fatty acid ester.

20. A method of removing makeup from skin comprising applying the makeup remover pad of claims 1, 8, or 16 without pre-moistening the pad with water to a coating of makeup comprising a wax base, on said skin.

* * * * *

UNITED STATES PATENT AND TRADEMARK OFFICE
CERTIFICATE OF CORRECTION

PATENT NO. : 4,806,572

DATED : February 21, 1989

INVENTOR(S) : George W. Kellett

It is certified that error appears in the above-identified patent and that said Letters Patent is hereby corrected as shown below:

At Col. 7, line 56 for "ixture" read --mixture--.

At Col 10, line 61, for "wieght" read --weight--.

At Col. 11, line 4, for "to¹uene" read --toluene--.

At Col. 11, line 6, "mEeq/g" read --mEq/g--.

Signed and Sealed this

Thirteenth Day of March, 1990

*Attest:*

JEFFREY M. SAMUELS

*Attesting Officer*  *Acting Commissioner of Patents and Trademarks*